United States Patent
Edlauer et al.

(10) Patent No.: US 8,861,828 B2
(45) Date of Patent: Oct. 14, 2014

(54) SHIFT COMPENSATION IN MEDICAL IMAGE PROCESSING

(75) Inventors: Martin Edlauer, Munich (DE); Brian Vasey, Munich (DE)

(73) Assignee: Brainlab AG, Feldkirchen (DE)

( * ) Notice: Subject to any disclaimer, the term of this patent is extended or adjusted under 35 U.S.C. 154(b) by 201 days.

(21) Appl. No.: 13/500,969

(22) PCT Filed: Nov. 26, 2009

(86) PCT No.: PCT/EP2009/065916
§ 371 (c)(1),
(2), (4) Date: Apr. 9, 2012

(87) PCT Pub. No.: WO2011/063840
PCT Pub. Date: Jun. 3, 2011

(65) Prior Publication Data
US 2012/0195487 A1    Aug. 2, 2012

(51) Int. Cl.
*G06K 9/00* (2006.01)
*G01R 33/563* (2006.01)
*G06T 7/00* (2006.01)
*A61B 5/055* (2006.01)
*A61B 19/00* (2006.01)
*G01R 33/48* (2006.01)

(52) U.S. Cl.
CPC . *G01R 33/56341* (2013.01); *G06T 2207/30016* (2013.01); *A61B 5/055* (2013.01); *A61B 2019/5287* (2013.01); *A61B 19/20* (2013.01); *G06T 2207/10088* (2013.01); *G06T 7/0028* (2013.01); *G06T 2207/30204* (2013.01); *G01R 33/4828* (2013.01); *Y10S 128/922* (2013.01); *Y10S 128/923* (2013.01)
USPC ........... 382/131; 382/128; 382/132; 382/278; 128/922; 128/923

(58) Field of Classification Search
USPC ................ 382/128, 130, 131, 132, 278, 291; 128/922, 923
See application file for complete search history.

(56) References Cited

U.S. PATENT DOCUMENTS

| 4,857,847 A | 8/1989 | Machida |
| 5,134,372 A | 7/1992 | Inoue |

(Continued)

FOREIGN PATENT DOCUMENTS

| DE | 37 31 473 | 4/1988 |
| EP | 0 146 905 A2 | 7/1985 |

(Continued)

OTHER PUBLICATIONS

International Search Report for International Application No. PCT/EP2009/065916 dated Jul. 14, 2010.

(Continued)

*Primary Examiner* — Yosef Kassa
(74) *Attorney, Agent, or Firm* — Tucker Ellis LLP

(57) ABSTRACT

The invention relates to a method for positionally correlating, with computer assistance, patient image information included in image data generated by a magnetic resonance scanner and fiducial patient markers represented in the image data, wherein a positional relationship between the patient image information and the fiducial markers is determined by taking into consideration at least the following parameters: a) the material properties of the fiducial markers; b) image generation data included in the image data or provided with the image data; c) the resonance frequency recording mode of the magnetic resonance scanner; and d) any relative positional shift between the patient data and the fiducial markers resulting from the combination of the parameters a) to c). The invention also relates to the use of such a positional correlation in a method for registering patient image data and in a method for navigationally assisting a medical procedure.

15 Claims, 2 Drawing Sheets

(56) References Cited

U.S. PATENT DOCUMENTS

| | | | |
|---|---|---|---|
| 5,545,993 | A | 8/1996 | Taguchi et al. |
| 6,459,922 | B1 | 10/2002 | Zhang |
| 6,678,703 | B2 * | 1/2004 | Rothschild et al. .................. 1/1 |
| 8,155,417 | B2 * | 4/2012 | Piron et al. .................... 382/131 |
| 8,311,791 | B1 * | 11/2012 | Avisar ............................ 703/11 |
| 8,345,940 | B2 * | 1/2013 | Mattiuzzi et al. ............. 382/128 |
| 8,396,268 | B2 * | 3/2013 | Zabair et al. .................. 382/128 |
| 8,509,513 | B2 * | 8/2013 | Piron et al. .................... 382/131 |
| 8,520,920 | B2 * | 8/2013 | Guehring et al. ............. 382/128 |
| 8,532,359 | B2 * | 9/2013 | Takanami et al. ............. 382/131 |
| 8,542,900 | B2 * | 9/2013 | Tolkowsky et al. ........... 382/130 |
| 8,634,626 | B2 * | 1/2014 | Shi et al. ....................... 382/131 |
| 2001/0010810 | A1 | 8/2001 | Miyoshi |
| 2004/0032977 | A1 | 2/2004 | Blezek et al. |

FOREIGN PATENT DOCUMENTS

| | | |
|---|---|---|
| EP | 0 174 502 A2 | 3/1986 |
| EP | 0337588 | 10/1989 |
| EP | 0339090 | 11/1989 |

OTHER PUBLICATIONS

Sumanaweera T S et al., "MR geometric distortion correction for improved frame-based stereotaxic target localization accuracy.", Magnetic Resonance in Medicine: Official Journal of the Society of Magnetic Resonance in Medicine/Society of Magnetic Resonance in Medicine, Jul. 2005, vol. 34, No. 1, pp. 106-113.

EPC Communication pursuant to Article 94(3) dated Mar. 27, 2014.

Derek Hill et al., "Registration of MR and CT Images for Clinical Applications", Medical Image Registration, Jun. 27, 2001, vol. 5, pp. 217-232.

\* cited by examiner

SHIFT COMPENSATION IN MEDICAL IMAGE PROCESSING

This application is a national phase of International Application No. PCT/EP2009/065916 filed Nov. 26, 2009 and published in the English language.

The present invention relates to the technical field of medical image processing. In particular, it relates to compensating for a positional shift by elements in medical images generated by a magnetic resonance scanner or "MR scanner". While the accuracy with which absolute positions or relative positions of certain elements are displayed in MR images may not be of the utmost importance in applications in which a physician merely needs to determine whether certain structures are present in the image or the characteristics which they exhibit, absolute positions and positional relationships between image elements are very important in applications such as image-guided surgery, image-guided radiotherapy or in medical navigation in general.

In technical terms, magnetic resonance imaging is based on the fact that 1H protons in an object, when exposed to a very strong magnetic field, can absorb and emit energy at a distinct frequency known as the Larmor frequency. The Larmor frequency depends on the magnetic field strength and the molecular bond of the proton within the molecule. The so-called fat-water shift is a phenomenon resulting from the fact that a 1H proton bonded in water has a different Larmor frequency to a 1H proton bonded in a molecule of fat. Since MRI (Magnetic Resonance Imaging) protocols use frequency encoding to locate the position of a molecule when imaged, the above-mentioned difference in Larmor frequencies has the effect that two objects in identical positions, one containing water and the other containing fat, would exhibit a shift with respect to each other in the magnetic resonance image, i.e. would be shown at different positions.

The magnitude of such a fat-water shift is proportional to the magnetic field strength employed. In a 1.5 T (Tesla) MR scanner, the resonance frequency of the 1H proton in fat is about 220 Hz higher than that of the 1H proton in water. Since the trend is towards higher magnetic field strengths, the fat-water shift is becoming an ever more prominent phenomenon.

An MR scanner is typically tuned to water, hence a water object in its isocenter will appear in the isocenter of the acquired image, whereas the same object would be shifted away from the isocenter if it contained a fat. As mentioned above, this fat-water shift is especially problematic when using MR images in image-guided surgery systems or medical navigation systems, since the images generated have to be registered before navigation can be performed on the basis of the image data. The aim of registration is to find a transformation between the image space and a coordinate system used in medical navigation, for example a patient coordinate system which is usually defined by a tracking reference attached to the patient and tracked by a tracking system (for example a camera system) associated with the medical navigation system. The transformation matrix can be found by correlating points in the patient space with points in the image space (so-called pair-point registration). In order to simplify registration and improve its accuracy, fiducial markers are used and placed on the patient before performing magnetic resonance imaging.

With regard to frequency encoding, MR scanners are—as mentioned above—in most cases tuned to water, i.e. they are configured such that water markers (fiducials) or water objects would be imaged at the correct position. Thus, such a water object or water marker imaged by a "water-tuned" MR imaging system would enable correct registration, whereas a marker containing fat, for example an oil, would render registration inaccurate because of the fat-water shift. In general, and irrespective of the technical specifics of finding the transformation matrix, registration will be biased towards either fat or water, depending on the substance used to find the transformation matrix. Hence, any navigation based on this registration will either be accurate for water or for fat but never for both.

In order to deal with the problems caused by the fat-water shift, efforts have been made to provide an elimination procedure by adapting the scanning procedure itself, for example by changing the scan parameters. Pulse sequences have for example been adapted so as to enable a compensation of the fat-water shift by producing two sets of images with opposite shift directions and using this information to correct the shift. These sequences require considerable longer scan times then regular sequences. However, long pulse sequences are on the one hand less acceptable to patients than short sequences, and on the other hand, the trend within this field of technology is towards employing higher magnetic field strengths. Thus, the fat-water shift becomes a serious problem.

It is an object of the present invention to provide a solution to the aforementioned problems. In particular, the present invention aims to enable correct registration for medical navigation purposes on the basis of magnetic resonance imaging data generated using current modern MR scanners.

The above object is achieved by a method for positionally correlating patient image information and fiducial patient markers, with computer assistance, in accordance with claim 1. The sub-claims define advantageous embodiments of this method and other aspects of the present invention which employ this method, such as a registration method or a medical navigation method.

In accordance with the present invention, a method is provided for positionally correlating, with computer assistance, patient image information included in image data generated by a magnetic resonance scanner and fiducial patient markers represented in the image data, wherein a positional relationship between the patient image information and the fiducial markers is determined by taking into consideration at least the following parameters:
a) the material properties of the fiducial markers;
b) image generation data included in the image data or provided with the image data;
c) the resonance frequency recording mode of the magnetic resonance scanner; and
d) any relative positional shift between the patient data and the fiducial markers resulting from the combination of the parameters a) to c).

After such a positional correlation has been determined, the information required in order to eliminate any errors or inaccuracies originating from scanning different materials is available. Thus, on the basis of this available information, any additional steps to be taken or applications to be performed can be initiated on the basis of correct positional assumptions and will thus deliver correct results.

In other words, the present invention provides a method which increases the accuracy of applications based on magnetic resonance images, such as image-guided surgery, image-guided radiotherapy or other navigationally assisted procedures. This is particularly true of applications involving a method for finding a transformation matrix between the image space and a second space, for example the coordinate system of a camera used to track the patient and/or instruments, the patient coordinate system or the coordinate system of a treatment device such as an accelerator which is used for radiotherapy treatments. Any registration procedure as mentioned above can be carried out directly and accurately using the information provided by the method in accordance with the present invention, such that any shift by objects in the images will not impair registration, navigation or treatment. This will substantially increase the accuracy of navigation and enable fiducials of different materials, for example both water and fat fiducials, to be accurately navigated. Any kind of MR markers can then be used in available hardware devices, and fiducial markers could easily be exchanged without affecting the registration procedure, which in turn could therefore be easily switched to a different base material, for example water or fat, as required.

The material of the fiducial markers can comprise fat or water, and the positional relationship can be determined by taking into consideration the relative positional shift which occurs when the resonance frequency recording mode of a magnetic resonance scanner is tuned to water or fat, respectively, and vice versa.

In one embodiment of the method according to the present invention, the image generation data comprises information about the field strength, the pixel bandwidth and the pixel size as well as the frequency encoding direction of a magnetic resonance scanner. This information can in particular be included in the DICOM header of the image(s) generated by the magnetic resonance scanner.

The navigation system or the computer system which processes the information concerning the positional correlation as provided by the present invention must be able to in some way associate the aforementioned image generation data with a respective image, hence image generation data can either be provided with the image or separate from the image but in such a way that it can be associated with said image without incurring an error. Magnetic resonance images usually have a so-called DICOM header which contains a set of information, for example patient information and image generation information. For the purpose of correlating positions in accordance with the present invention, it is of course highly advantageous that all of the information needed, as detailed above, is usually present in the DICOM header. Thus, a navigation system or a computer system performing the present invention merely needs to be provided with the usual magnetic resonance image data and will still have all of the information needed to find the correct positional correlation between the patient image data and the fiducial markers, irrespective of the "material tuning" of the devices used.

The image generation data can also comprise information on the field-of-view and/or matrix size of the magnetic resonance scanner, wherein this information is in particular included in the DICOM header of the image(s) generated by the magnetic resonance scanner.

It is possible to determine the positional shift for fat and water (FWS) contained in the fiducial materials as follows:

$$FWS_F = \frac{220 \text{ Hz}}{1.5T} B_0$$

$$FWS_P = \frac{FWS_F}{BW_P}$$

$$FWS_{mm} = FWS_P \cdot P_S$$

where:
$FWS_F$ is the fat-water shift in Hz;
$FWS_P$ is the fat-water shift in pixels;
$FWS_{mm}$ is the fat-water shift in mm;
$B_0$ is the magnetic field strength in Tesla;
$BW_P$ is the pixel bandwidth in Hz; and
$P_S$ is the pixel size in mm.

In one embodiment, the direction of the positional shift can be determined in relation to the frequency encoding direction of the magnetic resonance scanner.

In accordance with another embodiment of the present invention, the actual positional relationship between the parts of the patient's body as represented in the patient image information and the fiducial markers is determined by correcting the positional shift in the fiducial markers with respect to the parts of the patient's body, depending on the material of the markers and the resonance frequency recording mode of the magnetic resonance scanner. In other words, this version of the method in accordance with the invention compensates for the positional shift and provides an image with fiducial markers shown at the correct locations on the patient's body.

Another aspect of the present invention relates to a method for registering patient image data generated by a magnetic resonance scanner within a predetermined coordinate system by means of fiducial patient markers represented in the image data, wherein the patient image positional information and the positional information on the fiducial markers is correlated using any of the methods mentioned and specified herein, in particular above. Any such registration will be made accurate and correct because it is based on known positional correlations. The patient image data can be registered in this way by means of fiducial markers on the basis of marker position data which is corrected or shifted in accordance with the determined positional relationship and by taking into account any positional shift present.

Another aspect of the present invention is directed to a method for navigationally assisting a medical procedure by displaying patient images included in a patient image data set generated by a magnetic resonance scanner, on a navigation display, wherein the patient image data set is registered in the navigation coordinate system by a registration method as mentioned herein and in particular above. The main advantage of such navigation will of course be its accuracy and reliability, since it is based on an accurate and correct registration.

In such a navigationally assisted medical procedure, shifted positions of the parts of the patient's body as represented in the patient image information can be displayed in accordance with a positional correction which is performed on the basis of the correlated positions of the patient image data and the fiducial markers. Alternatively or in addition to the above-defined feature, shifted positions of the fiducial markers can be displayed in accordance with a positional correction which is performed on the basis of the correlated positions of the patient image data and the fiducial markers, i.e. since the information about the correlated positions is available, the user has the choice of displaying correctly shifted markers or correctly shifted parts of the patient's body or both, as required by the application.

In another embodiment, the registered positions of the parts of the patient's body as represented in the patient image information in accordance with more than one resonance frequency recording mode of the magnetic resonance scanner are made available to the navigation system. For example, both fat-tuned and water-tuned image data can be provided to the navigation system. The suitable registered position of the parts of the body (in accordance with the resonance frequency recording mode of the magnetic resonance scanner) can then be automatically displayed by the navigation system, wherein the suitability of the registered position is determined by the navigation system by analyzing the material properties of the patient body part tissue and associating it with the registration to be employed. In other words, depending on the tissue material detected, the navigation system can choose and display the most suitable "material-tuned" (for example water-tuned or fat-tuned) image to be provided for correct registration.

The invention also relates to a program which, when it is running on a computer or is loaded onto a computer, causes the computer to perform a method as defined herein, and to a computer program storage medium which comprises such a computer program.

The invention will be explained below in greater detail with reference to particular embodiments and to the attached drawings. It should be noted that each of the features of the present invention referred to herein can be implemented separately or in any expedient combination. In the drawings.

Figure 1:
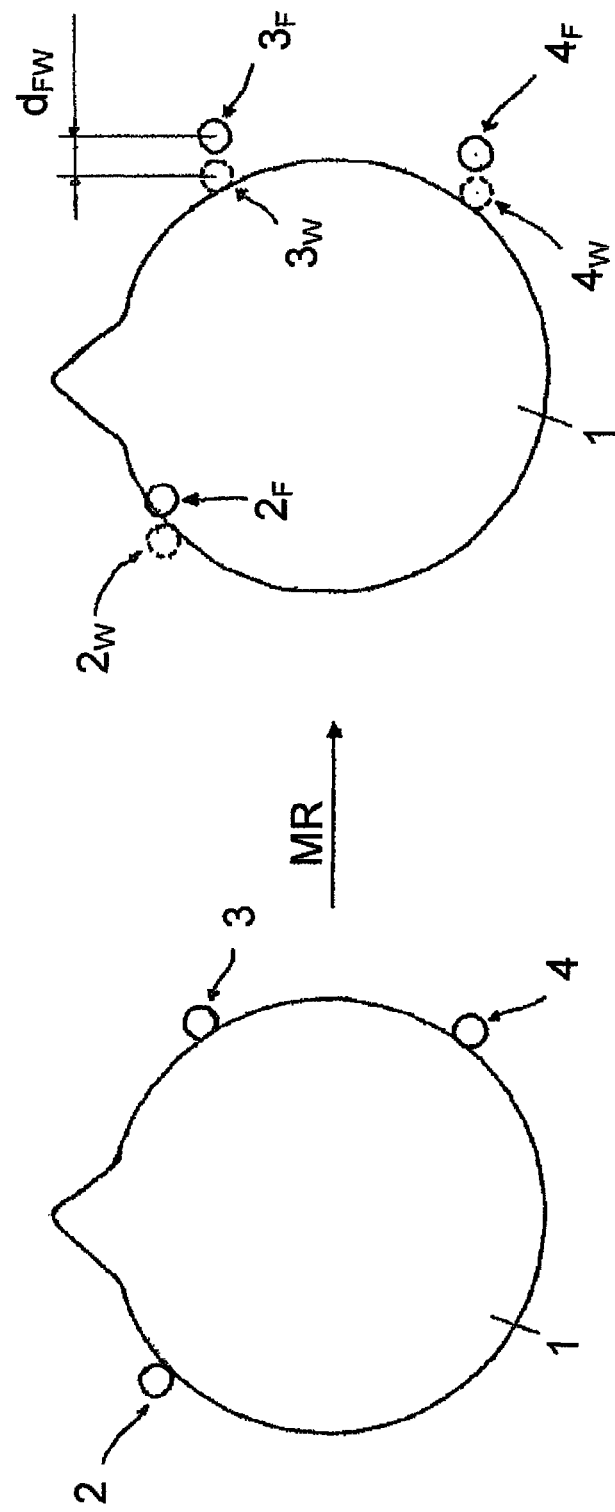
FIG. 1 illustrates, in general, the fat-water shift in an MR image.

The fat-water shift which occurs in magnetic resonance imaging shall now be explained with reference to FIG. 1. In the left-hand representation in FIG. 1, a schematic view of a patient's head 1 as seen from above is shown in a single slice image which is part of an image data set produced using a magnetic resonance scanner. Thus, the shape of the patient's head, as indicated by the reference numeral 1, constitutes patient image information in accordance with the terminology employed herein. The left-hand representation in FIG. 1 also shows fiducial markers 2, 3 and 4 which are attached to the contour of the head 1.

It will now be assumed that the markers 2, 3 and 4 are fat-based markers, for example markers comprising spheres containing an oil which can be imaged by an MR scanner. If, however, an MR scanner is used which is "water-tuned", i.e. which operates in a resonance frequency recording mode which is adjusted to the Larmor frequency of water, then an image as shown in continuous lines on the right-hand side in FIG. 1 will be created, i.e. the fat-based markers 2, 3, 4 will be positionally determined incorrectly with respect to the contour 1 (which for its part would be imaged on the basis of its water content). Thus, the images $2_F$, $3_F$ and $4_F$ of the markers are shown as having shifted away from the contour 1 by a certain distance or relative positional shift $d_{FW}$. This positional shift $d_{FW}$ is shown on the right-hand side in FIG. 1 by virtual markers $2_W$, $3_W$ and $4_W$ which are shown in dashed lines. These fiducial marker images $2_W$, $3_W$ and $4_W$ are shown at the locations where the real markers should have been imaged, namely attached to the contour of the head 1. Another interpretation would be that the markers $2_W$, $3_W$ and $4_W$ would have been the correct marker images if, instead of fat-based markers, markers with a water content had been used as the markers 2, 3 and 4 and a water-tuned magnetic resonance imaging procedure had been performed.

The invention addresses these problems by providing a way of finding the positional correlation between the patient image 1 and the fiducial markers 2, 3 and 4. To this end, it has proved highly advantageous that scan parameters are usually provided together with the image data when magnetic resonance scans are produced, i.e. the DICOM header of a magnetic resonance scan image, for example, would comprise a range of information about the patient and the scan parameters, in addition to the image data itself. As shown in the following table, this information can include:

| Scan parameter | DICOM information |
| --- | --- |
| field strength: $B_0$ | ([0018, 0087] - MagneticFieldStrength) |
| pixel bandwidth: $BW_P$ | ([0018, 0095] - PixelBandwidth) |
| pixel size: $P_S$ | ([0028, 0030] - PixelSpacing) |

With this information available to it, a computer-assisted system such as a medical navigation system which is using the magnetic resonance images as a basis for image-guided surgery will be able to calculate the fat-water shift as follows:

$$FWS_F = \frac{220 \text{ Hz}}{1.5T} B_0$$

$$FWS_P = \frac{FWS_F}{BW_P}$$

$$FWS_{mm} = FWS_P \cdot P_S$$

where:
$FWS_F$ is the fat-water shift in Hz;
$FWS_P$ is the fat-water shift in pixels;
$FWS_{mm}$ is the fat-water shift in mm;
$B_0$ is the magnetic field strength;
$BW_P$ is the pixel bandwidth; and
$P_S$ is the pixel size.

Following this calculation, the fat-water shift will have been quantified.

It is also possible to determine the direction of the fat-water shift from information in the DICOM header. This information could for example read as follows: ([0018,1312]—In-PlanePhaseEncodingDirection). It can be deduced from this data that the frequency encoding direction is oriented at exactly a 90° angle to the phase encoding direction defined by [0018,1312]. The latter two values can assume the values ROW or COL, i.e. the phase encoding can be oriented along rows or columns, and the frequency encoding will be oriented accordingly.

Thus, from a few simple calculations using data already available, the present invention makes it possible to exactly calculate the fat-water shift and thus to obtain a positional correlation between the patient image and the fiducial markers for all of the following possible scenarios: the part of the patient's body contains fat or water; the MR scanner is tuned to fat or water; and the fiducial markers contains fat or water. Thus, if the latter parameters can be established for any situation (which should be possible, since the user will know which body parts are being imaged using which MR scanner, and the kind of fiducial markers being used), any problems arising from a fat-water shift can be precisely corrected or eliminated.

Figure 2:
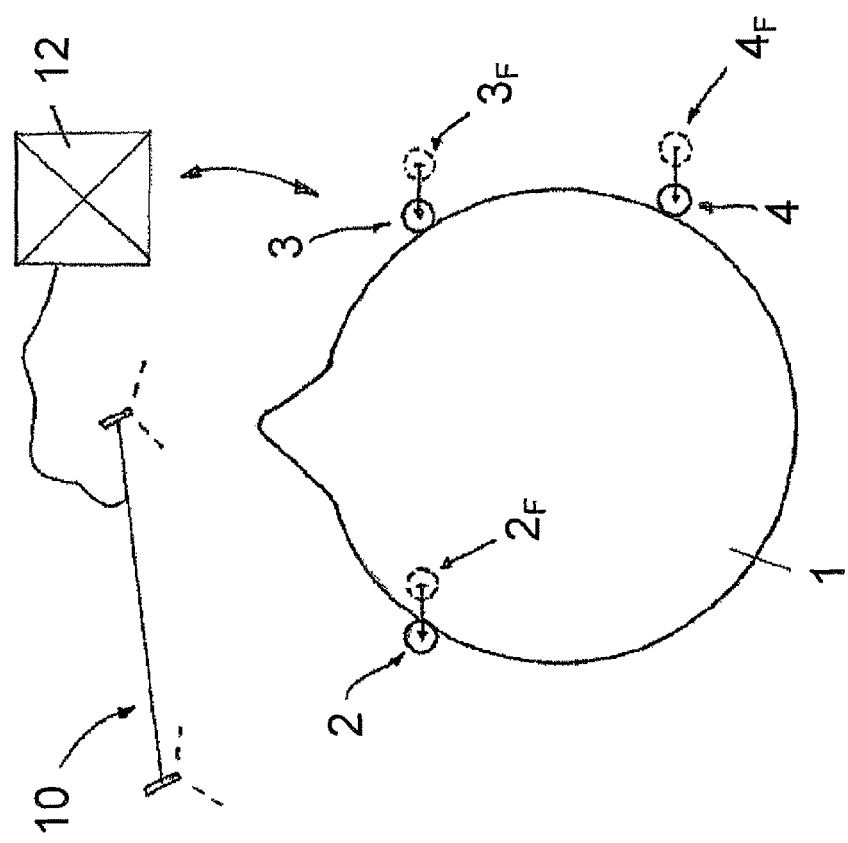
FIG. 2 illustrates an embodiment of the present invention comprising marker position correction.

One example of performing such a correction is shown in FIG. 2, in which a patient's head 1 has been imaged together with fat-based fiducial markers $2_F$, $3_F$ and $4_F$ using a scanner in a water-tuned mode. As a result, an image display of this magnetic resonance image which has not yet been corrected would show the markers in the positions $2_F$, $3_F$ and $4_F$ indicated by dashed lines. However, in accordance with this aspect of the invention, the information available in the DICOM header is used to calculate the fat-water shift. The positions of the registration markers to be displayed are then shifted accordingly, such that the markers are then shown at their correct locations 2, 3 and 4. A registration procedure can then be performed on the basis of these marker positions 2, 3 and 4, for example a pair-point registration using a camera-based medical tracking system 10 connected to a medical navigation system 12, which are both only shown schematically in FIG. 2.

In most cases, an image as shown in FIG. 2 will be graphically set up by the graphics engine of the medical navigation system 12, such that once the marker positions have been corrected and shifted, more data will be exchanged between the display and the navigation system 12 while the registration procedure is performed on the basis of the corrected marker locations, wherein this data exchange is indicated in FIG. 2 by the double-headed arrow. Once registration is complete, a navigationally assisted medical treatment can be performed, wherein instruments and the patient can be positionally tracked by the tracking system 10.

Figure 3:
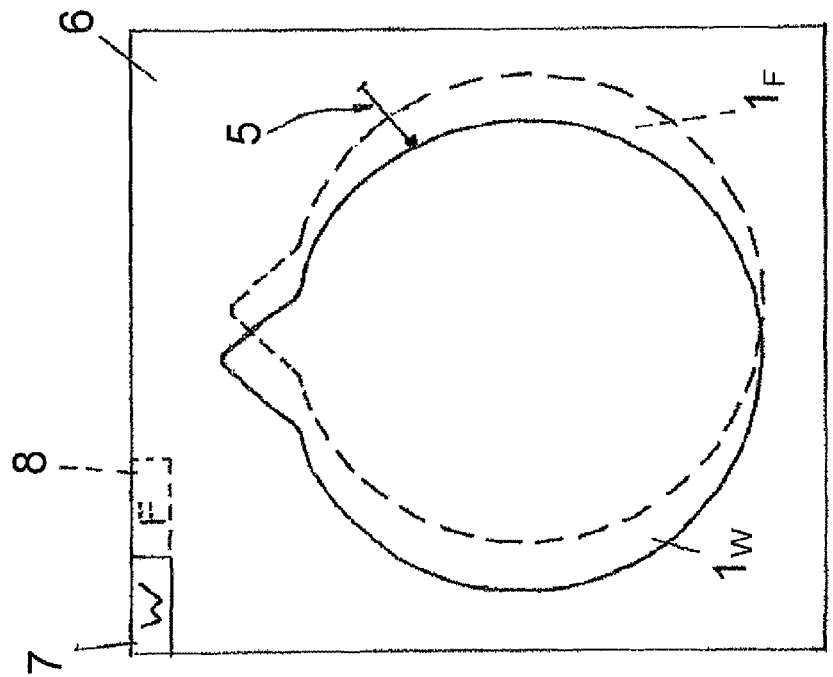
FIG. 3 shows a display of a medical navigation system with the option of shift-compensation.

Another embodiment, shown schematically in FIG. 3, advantageously uses the present invention. FIG. 3 shows a navigation display, for example a display of a navigation system 12 (FIG. 2). As explained above, an MR image of a patient's head 1 has been produced, and the fat-water shift has been calculated by taking into account the teachings of the present invention, such that the navigation system possesses information about the image position of the head in a water-based imaging mode ($1_W$) and a fat-based imaging mode ($1_F$). During navigation, an instrument 5 can be tracked and displayed on the navigation display. The instrument 5 is shown to have a tip pointing directly onto the outer contour of the patient's head, as is the case in the actual environment of the operating theater. Thus, the user would choose the button 7 marked W in order to use a water-based position correlation, so that the correct positional relationship between the instrument 5 and the contour 1 is displayed. The dashed line shows the contour $1_F$ which can be chosen by pressing the (software) button F marked by the reference numeral 8. In the present case, however, this would show an incorrect positional correlation between the instrument 5 and the contour 1 of the patient's head. On the other hand, if an image were taken of a body part consisting mainly of fat, and a fat-tuned imaging system had been used, it would be better to switch the display to the fat-based system using the button 8, which would show a more accurate instrument position (Fat on a fat-tuned MR would be displayed correctly, fat on a water-tuned MR would be displayed incorrectly). Thus, the software function allows the user to switch between water-based and fat-based registration, in order to provide more suitable assistance.

Another possible embodiment (not shown) uses the brightness value of weighted images, namely the so-called T1 or T2 weighted images in which fat and/or water appears brighter in the image. In this case, the software can automatically determine whether the tissue to be navigated is mostly fat or mostly water, and the bias incorporated into the registration procedure can be automatically changed from water-tuned to fat-tuned or vice versa, in order to display the correct positional correlation by means of the present invention.

The invention claimed is:

1. A method for positionally correlating, with computer assistance, patient image information included in image data generated by a magnetic resonance scanner and fiducial patient markers represented in the image data, such that a positional relationship between the patient image information and the fiducial markers is determined by taking into consideration at least the following parameters:
    a) the material properties of the fiducial markers;
    b) image generation data included in the image data or provided with the image data;
    c) the resonance frequency recording mode of the magnetic resonance scanner; and
    d) any relative positional shift between the patient data and the fiducial markers resulting from the combination of the parameters a) to c).

2. The method according to claim 1, wherein the material of the fiducial markers comprises fat or water, and the positional relationship is determined by taking into consideration the relative positional shift which occurs when the resonance frequency recording mode of the magnetic resonance scanner is tuned to water or fat, respectively, and vice versa.

3. The method according to claim 1, wherein the image generation data comprises information about the field strength, the pixel bandwidth or pixel size and the frequency encoding direction of the magnetic resonance scanner, wherein this information is in particular included in the DICOM header of the image(s) generated by the magnetic resonance scanner.

4. The method according to claim 1, wherein the image generation data also comprises information on the field-of-view and/or matrix size of the magnetic resonance scanner, wherein this information is in particular included in the DICOM header of the image(s) generated by the magnetic resonance scanner.

5. The method according to claim 1, wherein the positional shift for fat and water contained in the fiducial materials (FWS) is determined as follows:

$$FWS_F = \frac{220 \text{ Hz}}{1.5T} B_0$$

$$FWS_P = \frac{FWS_F}{BW_P}$$

$$FWS_{mm} = FWS_P \cdot P_S$$

where:
    $FWS_F$, is the fat-water shift in Hz;
    $FWS_P$ is the fat-water shift in pixels;
    $FWS_{mm}$ is the fat-water shift in mm;
    $B_0$ is the magnetic field strength;
    $BW_P$ is the pixel bandwidth; and
    $P_S$ in the pixel size.

6. The method according to claim 1, wherein the direction of the positional shift is determined in relation to the frequency encoding direction of the magnetic resonance scanner.

7. The method according to claim 1, wherein the actual positional relationship between the parts of the patient's body as represented in the patient image information and the fiducial markers is determined by correcting the positional shift in the fiducial markers with respect to the parts of the patient's body depending on the material of the marker and the resonance frequency recording mode of the magnetic resonance scanner.

8. A method for registering patient image data generated by a magnetic resonance scanner within a predetermined coordinate system by means of fiducial patient markers represented in the image data, characterized in that the patient image positional information and the positional information on the fiducial markers is correlated using the method of claim 1.

9. The method according to claim 8, wherein the patient image data are registered by means of the fiducial markers on the basis of marker position data which is corrected or shifted in accordance with the determined positional relationship and by taking into account the positional shift.

10. A method for navigationally assisting a medical procedure by displaying patient images included in a patient image data set generated by a magnetic resonance scanner, on a navigation display, characterized in that the patient image data set is registered in the navigation coordinate system by the registration method of claim 8.

11. The method according to claim 10, wherein shifted positions of the parts of the patient's body as represented in the patient image information are displayed in accordance with a positional correction which is performed on the basis of the correlated positions of the patient image data and the fiducial markers.

12. The method according to claim 10, wherein shifted positions of the fiducial markers are displayed in accordance with a positional correction which is performed on the basis of the correlated positions of the patient image data and the fiducial markers.

13. The method according to claim 10, wherein the registered positions of the parts of the patient's body as represented in the patient image information in accordance with more than one resonance frequency recording mode of the magnetic resonance scanner are made available to a navigation system, and wherein a suitable registered position in accordance with the resonance frequency recording mode of the magnetic resonance scanner is automatically displayed by the navigation system, wherein the suitability of the registered position is determined by the navigation system by analyzing the material properties of the patient body part tissue and associating it with the registration to be employed.

14. A computer program embodied on a non-transitory computer readable medium which, when it is running on a computer or is loaded onto a computer, causes the computer to perform a method for positionally correlating patient image information included in image data generated by a magnetic resonance scanner and fiducial patient markers represented in the image data, such that a positional relationship between the patient image information and the fiducial markers is determined by taking into consideration at least the following parameters:
   a) the material properties of the fiducial markers;
   b) image generation data included in the image data or provided with the image data;
   c) the resonance frequency recording mode of the magnetic resonance scanner; and
   d) any relative positional shift between the patient data and the fiducial markers resulting from the combination of the parameters a) to c).

15. A computer program storage medium which comprises a computer program according to claim 14.

\* \* \* \* \*